United States Patent [19]

Inman et al.

[11] Patent Number: 4,854,333

[45] Date of Patent: Aug. 8, 1989

[54] STABLE ANTIDANDRUFF SHAMPOO COMPOSITIONS

[75] Inventors: Everett Inman, Cincinnati, Ohio; Nancy J. Roberts, Baton Rouge, La.; Prem S. Juneja, Cincinnati, Ohio

[73] Assignee: The Procter & Gamble Company, Cincinnati, Ohio

[21] Appl. No.: 287,645

[22] Filed: Dec. 20, 1988

Related U.S. Application Data

[63] Continuation of Ser. No. 187,107, Apr. 28, 1988, abandoned.

[51] Int. Cl.$^4$ .................... A45D 7/00; A61K 7/06; A61K 33/40
[52] U.S. Cl. ............... 132/209; 424/DIG. 4; 424/70; 424/130; 424/616; 424/615; 424/702; 514/852; 514/880; 514/881; 132/202
[58] Field of Search ............ 514/852, 880, 881; 424/DIG. 4, 70, 130; 132/7

[56] References Cited

U.S. PATENT DOCUMENTS

| | | | |
|---|---|---|---|
| 122,986 | 11/1987 | McCall et al. | 252/174.017 |
| 148,728 | 1/1988 | McCall | 252/549 |
| 2,694,669 | 11/1954 | Baldwin et al. | 424/Dig. 4 |
| 3,152,046 | 10/1964 | Kapral | 424/DIG. 4 |

OTHER PUBLICATIONS

The Extra Pharmacopoeia, Pharmaceutical Press, 26th Ed., 1972, pp. 572-573.
Physician's Desk Reference for Non-Prescription Drugs, 4th Ed., 1983, p. 503.

*Primary Examiner*—Dale R. Ore
*Attorney, Agent, or Firm*—S. J. Goldstein; R. C. Witte

[57] ABSTRACT

Disclosed are selenium sulfide lotion shampoos containing peroxy oxidizing agents, such as hydrogen peroxide and sodium percarbonate. These compositions provide antidandruff efficacy and do not become discolored upon storage. A method for preparing color-stable selenium sulfide shampoo compositions is also taught.

26 Claims, No Drawings

STABLE ANTIDANDRUFF SHAMPOO COMPOSITIONS

This is a continuation of application Ser. No. 187,107 filed on Apr. 28, 1988, now abandoned.

TECHNICAL FIELD

This present invention is related to antidandruff shampoos containing selenium sulfide. These shampoos do not become discolored upon storage.

BACKGROUND OF THE INVENTION

Lotion shampoos are widely accepted due to their ease of use. They are easily applied to and spread through the hair. Frequently, such shampoos are used as a convenient vehicle to apply pharmaceutical actives to the scalp for the treatment of dandruff or seborrheic dermatitis. One such commonly used active is selenium sulfide (Martindale, The Extra Pharmacopoeia, Pharmaceutical Press, 26th ed., 1972, pp 572-573). While being effective in treating dandruff and seborrhea, selenium sulfide shampoos tend to discolor uponn storage, particularly at high temperatures, becoming a very non-aesthetic grey-green-black color. In 1954, it was found that selenium sulfide could be stabilized and the discoloration minimized by formulating the shampoo with a buffering system (U.S. Pat. No. 2,694,669, Baldwin et al., issued Nov. 16, 1954). This approach, however, presents several product formulation negatives, particularly in terms of decreased lathering and conditioning performance, as well as limiting the range of surfactants useful in the shampoos. Thus, it would be highly desirable to formulate a color-stable shampoo containing selenium sulfide, having a pH close to the neutral range.

It has been surprisingly found by the present inventors that when peroxy oxidizing agents, such as hydrogen peroxide or sodium percarbonate, are included or used in the preparation of selenium sulfide-containing shampoo compositions, those compositions provide antidandruff efficacy and color stability without requiring the use of a buffer system.

It is an object of the present invention, therefore, to provide color-stable selenium sulfide lotion shampoos.

It is a further object of the present invention to provide selenium sulfide lotion shampoos utilizing specifically defined oxidizing agents, including hydrogen peroxide and sodium percarbonate.

It is a further object of the present invention to provide a method, utilizing peroxy oxidizing agents, for preparing colorstable selenium sulfide lotion shampoos.

It is a still further object of the present invention to provide a method for shampooing hair with improved selenium sulfide compositions.

Unless otherwise indicated, all percentages and ratios herein are by weight. Additionally, all measurements are made at 25° C. in the composition or on the pure material, unless otherwise specified.

SUMMARY OF THE INVENTION

The present invention relates to shampoo compositions comprising from about 10% to about 30% of a synthetic surfactant, from about 0.005% to about 0.9% of a peroxy oxidizing agent, from about 0.1% to about 5.0% of particulate selenium sulfide having an average particle size of less than about 25 μm, and water.

The present invention also relates to a process for preparing an antidandruff shampoo product wherein particulate selenium sulfide (having an average particle size less than about 25 μm) is washed with an aqueous solution comprising from about 0.1% to about 30.0% of a peroxy oxidizing agent, the washing solution is removed from the selenium sulfide, and the selenium sulfide is mixed with other shampoo ingredients.

DETAILED DESCRIPTION OF THE INVENTION

Surfactant

An essential component of the present compositions is a surfactant. The surfactant, which may be selected from any of a wide variety of synthetic anionic, amphoteric, zwitterionic and nonionic surfactants, is present at a level of from about 10% to about 30%, preferably from about 15% to about 22%, most preferably from about 18% to about 20%, of the compositions. Mixtures of these surfactants may also be used.

Synthetic anionic surfactants can be exemplified by the alkali metal salts of organic sulfuric reaction products having in their molecular structure an alkyl radical containing from about 8-22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of about 1 mole of a higher fatty alcohol (e.g., tallow or coconut oil alcohols) and from about 1 to about 12 moles of ethylene oxide; sodium or potassium salts of alkyl phenol ethylene oxide ether sulfate with from about 1 to about 10 units of ethylene oxide per molecule and in which the alkyl radicals contain from about 8 to about 12 carbon atoms; sodium alkyl glyceryl ether sulfonates; the reaction product of fatty acids having from 10 to about 22 carbon atoms esterified with isethionic acid and neutralized with sodium hydroxide; and water soluble salts of condensation products of fatty acids with sarcosine.

Zwitterionic surfactants are exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

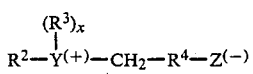

wherein $R^2$ is an alkyl, alkenyl, or hydroxy alkyl radical of from about 8 to about 28 carbon atoms, and contains from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing from about 1 to about 3 carbon atoms; x is 1 when Y is a sulfur atom, and 2 when Y is a nitrogen or phosphorus atom; $R^4$ is an alkylene or hydroxyalkylene of from about 1 to about 4 carbon atoms; and Z is a radical selected from the group consisting of carboxylate, sulfonate, sulfate, phosphonate, and phosphate groups.

Examples include: 4-[N,N-di(2-hydroxyethyl)-M-octadecylammonio]-butane-1-carboxylate; 5-[S-3-hydroxypropyl--hexadecylsulfonio]-3-hydroxypentane-1-sulfate; 3-[P,P-diethyl-P-3,6,9-trioxatetradecoxylphosphonio]-2-hydroxypropane-1-phosphate; 3-[N,N-dipropyl-N-3-dodecoxy-2-hydroxypropylammonio]-propane-1-phosphonate; 3-(N,N-dimethyl-N-hexadecylammonio)propane-1-sulfonate; 3-(N,N-dimethyl-N-hexadecylammonio)-2-hydroxypropane-1-sulfonate; 4-[N,N-di(2-hydroxyethyl)-N-(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and 5-[N,N-di(3-hydroxypropyl)-N-hexadecylammonio]-2-hydroxypentane-1-sulfate.

Other zwitterionics, such as betaines, are also useful in the present invention. Examples of betaines useful herein include the high alkyl bentaines, such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxy methyl betaine, stearyl bis-(2-hydroxypropyl) carboxymethyl betaine, oleyl dimethyl gamma-carboxypropyl betaine, and lauryl bis-(2-hydroxypropyl) alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amido betaines and amidosulfobetaines, wherein the $RCONH(CH_2)_3$ radical is attached to the nitrogen atom of the betaine, are also useful in this invention.

Examples of amphoteric surfactants which can be used in the compositions of the present invention are those broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate; sodium 3-dodecylaminopropane sulfonate; N-alkyltaurines, such as the one prepared by reacting dodecylamine with sodium isethionate according to the teaching of U.S. Pat. No. 2,658,072; N-higher alkyl aspartic acids, such as those produced according to the teaching of U.S. Pat. No. 2,438,091; and the products sold under the trade name "Miranol" and described in U.S. Pat. No. 2,528,378.

Nonionic surfactants, which are preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to about 12 carbon atoms in either a straight chain or branched chain configuration, with ethylene oxide, the said ethylene oxide being present in amounts equal to about 10 to about 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of about 2,500 to 3,000, are satisfactory.

3. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

4. Long chain tertiary amine oxides corresponding to the following general formula:

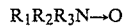

$$R_1R_2R_3N \rightarrow O$$

wherein $R_1$ is an alkyl, alkenyl or monohydroxyalkyl radical of from about 8 to about 18 carbon atoms, and contains from 0 to about 10 ethylene oxide moieties, and from 0 to 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyldodecylamine oxide, oleyldi(2-hydroxyethyl)amine oxide, dimethyloctylamine oxide, dimethyldecylamine oxide, dimethyltetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, and dimethylhexadecylamine oxide.

5. Long chain tertiary phosphine oxides corresponding to the following general formula:

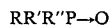

$$RR'R''P \rightarrow O$$

wherein R is an alkyl, alkenyl or monohydroxyalkyl radical of from about 8 to about 18 carbon atoms, and contains from 0 to about 10 ethylene oxide moieties, and from 0 to 1 glyceryl moiety, and R' and R'' are each alkyl or monohydroxyalkyl groups containing from about 1 to about 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide, 3,6,9-trioxactadecyldimethylphosphine oxide, cetyldimethylphosphine oxide, 3-dodecoxy-2-hydroxypropyldi(2-hydroxyethyl) phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)-phosphine oxide, dodecyldi(2-hydroxyethyl)-phosphine oxide, tetradecylmethyl-2-hydroxypropylphosphine oxide, oleyldimethylphosphine oxide, and 2-hydroxydodecyldimethylphosphine oxide.

6. Long chain dialkyl sulfoxides containing one short chain alkyl or hydroxyalkyl radical of from about 1 to about 3 carbon atoms (usually methyl) and one long hydrophobic chain which contains alkyl, alkenyl, hydroxyalkyl, or keto alkyl radicals containing from about 8 to about 20 carbon atoms, from 0 to about 10 ethylene oxide moieties, and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, and 3-hydroxy-4-dodecoxybutyl methyl sulfoxide.

Many additional nonsoap surfactants are described in McCUTCHEON'S, DETERGENTS AND EMULSIFIERS, 1986 Annual, published by Allured Publishing Corporation, which is incorporated herein by reference.

The above-mentioned surfactants can be used alone on in combination in the shampoo compositions of the present invention. The anionic surfactants, particularly the alkyl sulfates, the ethoxylated alkyl sulfates and mixtures thereof, as well as the isethionates, are preferred for use herein.

Oxidizing Agent

The shampoo compositions of the present invention contain from about 0.005% to about 0.9% of a peroxy oxidizing agent. It is this component which provides color stability to the compositions. Not every compound having oxidizing properties is useful in the present invention. Thus, metallic or anionic oxidizing agents, such as ferric chloride, potassium chlorate, and sodium hypochlorite, do not provide color stabilization in the context of the present invention. Examples of suitable peroxy oxidizing agents include hydrogen peroxide, sodium percarbonate, sodium perborate, perbenzoic acid, and other known peroxy acids. Mixtures of such peroxy oxidizing agents may also be used. Particularly preferred are hydrogen peroxide, used at a level of from about 0.005% to about 0.2%, especially from about 0.009% to about 0.15%, and sodium percarbonate, used at a level of from about 0.01% to about 0.8% of the composition.

Selenium Sulfide

Selenium sulfide is a staple item of commerce, and is wellknown for use in the treatment of dandruff and seborrhea. Selenium sulfide is generally regarded as a compound having one mole of selenium and two moles of sulfur. However, it may take the form of a cyclic structure, $Se_xS_y$, wherein $x+y=8$.

Selenium sulfide as provided by suppliers can be used in the present compositions provided the particle size of the selenium sulfide particles, on an average, is less than about 25 μm, preferably less than about 15 μm. These measurements are made using a forward laser light scattering device (e.g., a Malvern 360 instrument).

Selenium sulfide is present in the compositions of this invention at a level of from about 0.1% to about 5.0%, preferably from about 0.6% to about 2.5%.

Water

Water is the last essential component of the present invention and forms the remainder of the composition. It is generally present at a level of from about 20% to about 84%, preferably from about 60% to about 75%, of the composition.

Optional Components

A preferred optional component for use in the present invention is a suspending agent. The suspending agent can, for example, be any of several long chain acyl derivative materials or mixtures of such materials. Included are ethylene glycol esters of fatty acids having from about 16 to about 22 carbon atoms. Preferred are the ethylene glycol stearates, both mono- and distearate, but particularly the distearate containing less than about 7% of the monostearate. Still other suspending agents found useful are alkanol amides of fatty acids having from about 16 to about 22 carbon atoms, preferably about 16 to about 18 carbon atoms. Preferred alkanol amides are stearic monoethanolamide, stearic diethanolamide and stearic monoisopropanolamide. Still other long chain acyl derivatives include long chain esters of long chain fatty acids (e.g., stearyl stearate, cetyl palmitate), glyceryl esters (e.g., glyceryl distearate), and long chain esters of long chain alkanol amides (e.g., stearamide DEA distearate, stearamide MEA stearate).

Still other suitable suspending agents are alkyl ($C_{16-22}$) dimethyl amine oxides, such as stearly dimethyl amine oxide. If the compositions contain an amine oxide or a long chain acyl derivative as a surfactant, these components may also provide the suspending fuction and additional suspending agent may not be needed if the level of those materials are at least the minimum level described below.

Xanthan gum is another aspect used to suspend the selenium sulfide in the present compositions. This biosynthetic gum material is commerically available and is a heteropolysaccharide with a molecular weight of greater than 1 million. It is believed to contain D-glucose, D-mannose and D-glucuronate in the molar ratio of 2.8:2.0:2.0. The polysaccharide is partially acetylated with 4.7% acetyl. Supplemental information on these agents is found in Whistler, Roy L. (Editor), *Industrial Gums—Polysaccharides and Their Derivatives* New York: Academic Press, 1973. Kelco, a Division of Merck & Co., Inc., offers xanthan gum as Keltrol®.

A particularly preferred suspending system comprises a mixture of xanthan gum, present at a level of from about 0.05% to about 1.0%, preferably from about 0.2% to about 0.4%, of the compositions, together with magnesium aluminum silicate ($Al_2Mg_8Si_2$), present at a level of from about 0.1% to about 3.0%, preferably from about 0.5% to about 2.0%, of the compositions. Magnesium aluminum silicate occurs naturally in such smectite minerals as colerainite, saponite and sapphire. Refined magnesium aluminum silicates useful herein are readily available, for example as veegum, manufactured by R. T. Vanderbilt Company, Inc.

The suspending agent is present at a level of from about 0.1% to about 5.0%, preferably from about 0.5% to about 3.0%, of the compositions. The suspending agent serves to assist in suspending the selenium sulfide and may give pearlescence to the product. Mixtures of suspending agents are also suitable for use in the compositions of this invention.

Another preferred optional component for use in the present compositions is an amide. The amide used in the present compositions can be any of the alkanolamides of fatty acids known for use in shampoos. These are genrally mono- and diethanolamides of fatty acids having from about 8 to about 24 carbon atoms. Preferred are coconut monoethanolamide, lauric diethanolamide and mixtures thereof. The amide is present at a level of from about 1% to about 10% of the compositions.

The present compositions may also contain nonionic polymer material which is used at a low level to aid in keeping the particles of selenium sulfide dispersed. The material can be any of a large variety of types including cellulosic materials such as hydroxypropyl methyl cellulose, carboxymethyl cellulose, hydroxyethyl cellulose and sodium carboxymethyl cellulose, as well as mixtures of these materials. Other materials include alginates, polyacrylic acids, polyethylene glycol and starches, among many others. The nonionic polymers are discussed in detail in *Industrial Gums,* edited by Roy L. Whistler, Academic Press, Inc., 1973, and *Handbook of Water-Soluble Gums and Resins,* edited by Robert L. Davidson, McGraw-Hill, Inc., 1980. Both of these books in their entirety are incorporated herein by reference.

When included, the nonionic polymer is used at a level of from about 0.001% to about 0.1%, preferably from about 0.002% to about 0.05%, of the composition. Hydroxypropyl methyl cellulose is the preferred polymer.

Another suitable optional component useful in the present compositions is a nonvolatile silicone fluid.

The nonvolatile silicone fluid may be either a polyalkyl siloxane, a polyaryl siloxane, a polyalkylarly siloxane or a polyether siloxane copolymer and is present at a level of from about 0.1% to about 10.0%, preferably from about 0.5% to about 5.0%. Mixtures of these fluids may also be used and are preferred in certain executions. The dispersed silicone particles should also be insoluble in the shampoo matrix. This is the meaning of "insoluble" as used herein.

The essentially nonvolatile polyalkyl siloxane fluids that may be used include, for example, polydimethyl siloxanes with viscosities ranging from about 5 to about 600,000 centistokes at 25° C. These siloxanes are available, for example, from the General Electric Company as the Viscasil series and from Dow Corning as the Dow Corning 200 series. The siloxane viscosity can be measured by means of a glass capillary viscometer as set forth in Dow Corning Corporate Test Method CTM0004, July 20, 1970. Preferably the viscosity of these siloxanes range from about 350 centistokes to about 100,000 centistokes.

The essentially nonvolatile polyalkylaryl siloxane fluids that may be used include, for example, polymethylphenylsiloxanes having viscosities of from about 15 to about 30,000 centistokes at 25° C. These siloxanes are available, for example, from the General Electric Company as SF 1075 methyl phenyl fluoride or from Dow Corning as 556 Cosmetic Grade Fluid.

The essentially nonvolatile polyether siloxane copolymer that may be used is, for example, a polypropylene oxide modified dimethylpolysiloxane (e.g., Dow Corning DC-1248), although ethylene oxide or mixtures of ethylene oxide and propylene oxide may also be used.

Suitable silicone fluids are described in U.S. Pat. No. 2,826,551, Geen: U.S. Pat. No. 3,946,500, June 22, 1976, Drakoff; U.S. Pat. No. 4,364,837, Pader; and British Patent 849,433, Woolston. All of these patents are incorporated herein by reference. Also incorporated herein by reference is *Silicon Compounds,* distributed by Petrarch Systems, Inc., 1984. This reference provides a very good listing of suitable silicone materials.

Another silicone material found especially useful in the present compositions to provide good dry combing is a silicone gum. Silicone guns are described by Petrarch and others including U.S. Pat. No. 4,152,416, May 1, 1979, Spitzer, et al., and Noll, *Chemistry and Technology of Silicones,* New York, Academic Press, 1968. Useful silicone gums are also described in General Electric Silicone Rubber Product Data Sheets SE 30, SE 33, SE 54 and SE 76. All of these references are incorporated herein by reference. "Silicone gum" materials denote high molecular weight polydiorganosiloxanes having a mass molecular weight of from about 200,000 to about 1,000,000. Specific examples include polydimethylsiloxane, (polydimethylsiloxane) (methylvinylsiloxane) copolymer, poly(dimethylsiloxane) (diphenyl) (methylvinylsiloxane) copolymer, and mixtures thereof. Mixtures of silicon fluids and silicone guns are also useful herein.

The shampoos herein can contain a variety of other nonessential optional components suitable for rendering such compositions more formulatable, or aesthetically and/or cosmetically acceptable. Such conventional optional ingredients are well-known to those skilled in the art and include, e.g., preservatives, such as benzyl alcohol, methyl paraben, propyl paraben, and imidazolinidyl urea; cationic surfactants, such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; menthol; thickeners and viscosity modifiers, such as block polymers of ethylene oxide and propylene oxide such as Pluronic F88 offered by BASA Wyandotte, sodium chloride, sodium sulfate, propylene glycol, and ethyl alcohol; pH adjusting agents, such as citric acid, succinic acid, phosphoric acid, sodium hydroxide, sodium carobnate; perfumes; dyes; and sequestering agents, such as disodium ethylenediamine tetraacetate. Such agents generally are used individually at a level of from about 0.01% to about 10%, preferably from about 0.5% to about 5.0%, of the composition.

The pH of the present compositions is not critical and is generally in the range of from about 4 to about 7. However, one of the advantages of the present invention is that it permits the formulation of color-stable selenium sulfide shampoos at pH's around neutral, thereby providing improved performance and formulation flexibility.

Some representative methods for manufacturing the shampoo compositions of the present invention are described below in the Examples.

In a preferred method of manufacture, color-stable selenium sulfide shampoo compositions can be formulated without actually requiring inclusion of the oxidizing agent in the composition. In this process, the particulate selenium sulfide is thoroughly washed with an aqueous solution containing from about 0.1% to about 30%, preferably from about 2% to about 20%, of the peroxy oxidizing agents described above. Particularly preferred oxidizing agents for use in this process are hydrogen peroxide, sodium percarbonate, and mixtures thereof. The aqueous solution preferably additionally contains from about 0.5% to about 10%, preferably from about 1% to about 5%, of a surfactant. Preferred surfactants include sodium, potassium, ammonium, or triethanolamine alkyl sulfates, especially those obtained by sulfating the higher (e.g., $C_8$–$C_{18}$) alcohols. After the washing is complete, the aqueous solution is removed from the selenium sulfide by conventional means, such as filtration, decantation or centrifugation, and may be dried. The washed selenium sulfide is then used as the active component in a shampoo composition comprising:

(a) from about 10% to about 30% of a synthetic surfactant;

(b) from about 0.1% to about 5.0% of selenium sulfide having an average particle size of less then about 25 $\mu$m; and (c) from about 25% to about 84% water.

The present compositions are used in a conventional manner for cleaning hair. From about 0.1g to about 10g of the composition is applied to hair that has been wetted, generally with water, worked through the hair, and then rinsed out.

The following Examples further describe and demonstrate preferred embodiments within the scope of the present invention.

EXAMPLES I - II

The following compositions are representative of the present invention.

| | Weight % | | |
|---|---|---|---|
| Component | I | II | III |
| Silicone Premix | | | |
| Alkyl (ethoxy) sulfate (28% active) | 64.24 | 64.24 | 64.24 |
| Cetyl alcohol | 1.82 | 1.82 | 1.82 |
| Stearyl alcohol | 3.64 | 3.64 | 3.64 |
| Dimethicone (fluid/gum) | 30.30 | 30.30 | 30.30 |
| | 100.00 | 100.00 | 100.00 |
| EGDS Premix | | | |
| Water | 48.18 | 48.18 | 48.18 |
| Alkyl sulfate (25% active) | 28.28 | 28.28 | 28.28 |
| Cetyl alcohol | 0.81 | 0.81 | 0.81 |
| Stearyl alcohol | 0.13 | 0.13 | 0.13 |
| Coconut monoethanolamide | 6.75 | 6.75 | 6.75 |
| Ethylene glycol distearate (EGDS) | 6.75 | 6.75 | 6.75 |
| Tricetyl methyl ammonium chloride | 1.30 | 1.30 | 1.30 |
| Silicone premix | 7.45 | 7.45 | 7.45 |
| Preservative | 0.35 | 0.35 | 0.35 |
| | 100.00 | 100.00 | 100.00 |
| Methocel Premix | | | |
| Methocel (Hydroxypropyl methyl cellulose) | 3.33 | 3.33 | 3.33 |
| Water | 96.67 | 96.67 | 96.67 |
| | 100.00 | 100.00 | 100.00 |
| Selenium Sulfide Premix | | | |
| Water | 53.74 | 53.74 | 53.74 |
| Sodium citrate (38% active) | 0.95 | 0.95 | 0.95 |
| Citric acid (50% active) | 0.81 | 0.81 | 0.81 |
| Sodium alkyl sulfate | 4.00 | 4.00 | 4.00 |
| Preservative | 0.50 | 0.50 | 0.50 |
| Selenium sulfide (average particle size < 25 $\mu$m) | 25.00 | 25.00 | 25.00 |
| Methocel Premix | 15.00 | 15.00 | 15.00 |
| | 100.00 | 100.00 | 100.00 |
| Main Mix | | | |
| EGDS premix | 44.48 | 44.48 | 44.48 |
| Alkyl (ethoxy) sulfate (28% active) | 47.36 | 47.36 | 47.36 |
| Selenium sulfide premix | 4.00 | 4.00 | 4.00 |
| Water | 2.068 | 2.062 | 1.577 |
| Hydrogen peroxide | 0.009 | 0.015 | — |
| Sodium percarbonate | — | — | 0.50 |
| Ammonium xylene sulfonate | 1.40 | 1.40 | 1.40 |
| Fragrance | 0.65 | 0.65 | 0.65 |
| Preservative | 0.033 | 0.033 | 0.033 |
| | 100.000 | 100.000 | 100.000 |

The above compositions are prepared by heating all of the premixes except for the selenium sulfide premix in separate making containers to 71° C. and agitating them. The silicone premix is added to the EGDS premix, agitated, and then milled and cooled to 38° C. The methocel premix is added to the selenium sulfide premix with agitation. The EGDS and selenium sulfide premixes are combined with the remaining components to form the main mix.

These compositions, when used in the manner described in this application, provide the user with clean hair, as well as antidandruff efficacy. In addition, these compositions are colorstable, even after periods of storage.

Substantially similar results are obtained when the peroxy oxidizing agent used in Examples I–III is replaced, in whole or part, with an equivalent amount of sodium perborate, perbenzoic acid, and mixtures thereof.

EXAMPLES IV-V

| | Weight % | |
|---|---|---|
| Component | IV | V |
| DRO water | 66 | 56 |
| Sodium alkyl sulfate | 4 | 4 |
| Hydrogen peroxide | 5 | — |
| Sodium percarbonate | — | 15 |
| Selenium sulfide (average particle size < 25 $\mu$m) | 25 | 25 |

The above compositions are prepared at ambient conditions, agitating for one hour. The selenium sulfide is recovered by centrifugation and dried at 120° F. (49° C.). This material can then be used in the base formula described in Examples I–III, above, without adding the peroxy oxidizing agent (the oxidizing is replaced with water in the formulation). The resulting compositions are color-stable and provide the user with clean hair and antidandruff efficacy.

Substantially similar results are obtained where the peroxy oxidizing agent used in Examples IV and V is replaced, in whole or part, with an equivalent amount of sodium perborate, perbenzoic acid, and mixtures thereof.

What is claimed is:

1. A lotion dandruff shampoo composition comprising:
   (a) from about 10% to about 30% of a synthetic surfactant;
   (b) from about 0.1% to about 5.0% of selenium sulfide having an average particle size of less than about 25 $\mu$m;
   (c) from about 0.005% to about 0.9% of a peroxy oxidizing agent; and
   (d) from about 20% to about 84% water.

2. A shampoo composition according to claim 1 wherein the surfactant is selected from the group consisting of anionic surfactants, zwitterionic surfactants, amphoteric surfactants, and mixtures thereof.

3. A shampoo composition according to claim 2 wherein the peroxy oxidizing agent is selected from the group consisting of hydrogen peroxide, sodium percarbonate, sodium perborate, perbenzoic acid, and mixtures thereof.

4. A shampoo composition according to claim 3 wherein the surfactant is anionic.

5. A shampoo composition according to claim 4 wherein the anionic surfactant is selected from the group consisting of alkyl sulfates, ethoxylated alkyl sulfates, and mixtures thereof.

6. A shampoo composition according to claim 5 comprising from about 0.6% to about 2.5% of the selenium sulfide component.

7. A shampoo composition according to claim 6 wherein the peroxy oxidizing agent is hydrogen peroxide.

8. A shampoo composition according to claim 7 comprising from about 0.005% to about 0.2% of hydrogen peroxide.

9. A shampoo composition according to claim 8 comprising from about 0.009% to about 0.15% of hydrogen peroxide.

10. A shampoo composition according to claim 6 wherein the peroxy oxidizing agent is sodium percarbonate.

11. A shampoo composition according to claim 10 comprising from about 0.01% to about 0.8% of sodium percarbonate.

12. A shampoo composition according to claim 5 which additionally comprises from about 0.001% to about 0.1% of a nonionic polymer selected from the group consisting of hydroxypropyl methyl cellulose, carboxymethyl cellulose, sodium carboxymethyl cellulose, hydroxyethyl cellulose, and mixture thereof.

13. A shampoo composition according to claim 5 which additionally comprises from about 0.1% to about 10% of a nonvolatile silicone.

14. A shampoo composition according to claim 13 wherein the nonvolatile silicone is a mixture of silicone fluids and silicone gums.

15. A shampoo composition according to claim 5 which additionally comprises from about 0.1% to about 5% of a suspending agent.

16. A shampoo composition according to claim 15 wherein the suspending agent is ethylene glycol distearate.

17. A shampoo composition according to claim 15 wherein the suspending agent is a mixture of xanthan gum and magnesium aluminum silicate.

18. A shampoo composition according to claim 5 which additionally comprises from about 1% to about 10% of an amide.

19. A method of shampooing hair comprising applying to hair that has been wet with water from about 0.1 g to about 10 g of a composition according to claim 1, working the composition through the hair, and rinsing it from the hair.

20. A process for preparing a color-stable antidandruff shampoo composition comprising the steps of:
(a) washing selenium sulfide having an average particle size of less than about 25 $\mu$m with an aqueous solution comprising from about 0.1% to about 30% of a peroxy oxidizing agent;
(b) separating said aqueous solution from the selenium sulfide; and
(c) combining said selenium sulfide with shampoo ingredients to form a shampoo composition comprising:
(i) from about 10% to about 30% of a synthetic surfactant;
(ii) from about 0.1% to about 5.0% of said selenium sulfide; and
(iii) from about 20% to about 84% water.

21. A process according to claim 20 wherein the aqueous solution additionally comprises from about 0.5% to about 5% of a surfactant.

22. A process according to claim 21 wherein the surfactant is selected from the group consisting of sodium, potassium, ammonium, and triethanolamine alkyl sulfates, and mixtures thereof.

23. A process according to claim 21 wherein the peroxy oxidizing agent is selected from the group consisting of hydrogen peroxide, sodium percarbonate, sodium perborate, perbenzoic acid, and mixtures thereof.

24. A process according to claim 23 wherein the peroxy oxidizing agent is selected from the group consisting of hydrogen peroxide, sodium percarbonate, and mixtures thereof.

25. The color-stable antidandruff shampoo composition made according to the process of claim 20.

26. The color-stable antidandruff shampoo composition made according to the process of claim 24.

* * * * *